United States Patent [19]
Johnson

[11] Patent Number: 5,562,643
[45] Date of Patent: Oct. 8, 1996

[54] DEVICE AND TREATMENT FOR TREATMENT OF SKIN

[76] Inventor: James B. Johnson, 801 Rue Dauphine, Apt 339, Metairie, La. 70005

[21] Appl. No.: 221,475

[22] Filed: Apr. 1, 1994

Related U.S. Application Data

[63] Continuation-in-part of Ser. No. 997,453, Dec. 28, 1992, abandoned.

[51] Int. Cl.$^6$ .................................................. A61M 35/00
[52] U.S. Cl. ............................................ 604/290; 604/236
[58] Field of Search .......................... 604/73, 131, 181, 604/183, 236, 289, 290, 293, 248, 140, 141, 151, 164, 167, 189; 132/333; 424/62, 78.02, 78.05, 78.06, 78.07; 137/89, 98

[56] References Cited

U.S. PATENT DOCUMENTS

| | | | |
|---|---|---|---|
| 3,081,770 | 3/1963 | Hunter | 128/654 |
| 3,684,405 | 8/1972 | Wright et al. | 604/151 X |
| 3,804,097 | 4/1974 | Rudie | |
| 4,014,337 | 3/1977 | Treace | |
| 4,096,860 | 6/1978 | McLaughlin | |
| 4,671,790 | 6/1987 | Nishi | 604/131 |
| 4,729,401 | 3/1988 | Raines | 137/512 |
| 4,863,443 | 9/1989 | Hornung | 604/289 |
| 5,267,964 | 12/1993 | Karg | 604/141 |
| 5,308,343 | 5/1994 | Gafner | 604/289 |

FOREIGN PATENT DOCUMENTS 142390  10/1953  Sweden .

OTHER PUBLICATIONS

Brody, H. J., *Chemical Peeling*, pp. 1–22.

*Primary Examiner*—C. Fred Rosenbaum
*Assistant Examiner*—V. Alexander
*Attorney, Agent, or Firm*—Lynette Wylie

[57] ABSTRACT

A device and method for localized application of a fluid to a small area of skin, which includes an ejection nozzle forming a passage with one or more apertures, a receptacle chamber forming a cavity around the ejection nozzle, the receptacle chamber being configured and affixed to the ejection nozzle such that fluid ejected from the ejection nozzle is capable of being confined within the receptacle chamber, an inflow duct, and an outflow duct. Fluids which may be applied according to the present invention may include escharotic fluids, alpha-hydroxy compounds, exfoliants, cleansing agents, and other medicinal and cosmetic agents.

32 Claims, 4 Drawing Sheets

DEVICE AND TREATMENT FOR TREATMENT OF SKIN

This is a continuation of Application Ser. No. 07/997,453 for Device and Method For Treatment of Skin, which was filed on Dec. 28, 1992, now abandoned.

FIELD OF THE INVENTION

The device and method of this invention are drawn toward a treatment for skin by propelling a fluid on a confined area of skin. Applications of this invention may include delivery systems for a wide variety of agents, including escharotic agents, exfoliants, cleansing agents, and other cosmetic or medicinal agents.

BACKGROUND OF THE INVENTION

For many centuries, a variety of treatments and potions designed to treat skin problems of all types have been widely utilized. Numerous attempts to improve the appearance of skin by retardation, halting, or even reversal of the aging process have involved application of many different procedures and agents. For example, petroleum-based oils, creams, and solutions have, over the years, been topically applied in order to improve or prevent wrinkles, dryness, and to generally improve the appearance of skin. In addition, many compounds and solutions for fading various pigmented lesions resulting from exposure to sun and which typically worsen with age have been applied. The failure of such treatments to adequately address the desires of a populace concerned with the preservation of youthful-looking skin has led to the development of many cosmetic surgical procedures and high-technology cosmetic compounds which attempt to alleviate the effects of aging.

For over a century, physicians have been attempting to obliterate some of those undesired wrinkles and skin damage caused by exposure to sunlight, as well as scars and other skin problems, such as pigmentary dyschromias, by applying escharotic, or caustic peeling, agents to the skin. Since the early 1960's, the formulas and method for application of escharotic agents have been subject to sophisticated histologic studies and refined as such procedures have become more commonly utilized.

Escharotic agents for peeling skin which have been utilized over the years include phenol, resorcinol, salicylic acid, pyruvic acid, methyl salicylate, glycolic and other fruit-based or alpha-hydroxy acid, azelaic acid and trichloroacetic acid. Such escharotic agents have been used on various skin surfaces of the body in order to produce peeling designed to treat a diverse range of skin conditions, including scarring resulting from acne, bums, brasions or other skin injuries, pigmentary dyschromias, actinic keratoses, enlarged pores or philosebaceous follicles, rhytides, and more pronounced wrinkles, and other actinic damage to skin.

A peel applied to correct such skin problems is generally classified, according to the depth of the wound produced, as either superficial, medium-depth or deep-depth. Superficial wounding is defined as the wounding of portions of the epidermis alone or through the papillary dermis. Medium-depth wounding extends to the upper portion of the reticular dermis, and deep-depth wounding extends to the mid-reticular dermis. The depth of the peel administered is based on the indications of the particular skin condition being treated. Generally, although a superficial peel may be adequate for treatment of mild scarring and pigmentation dyschromias of the skin, deep peels are most effective for treatment of the majority of skin problems, such as deeper scarring, serious sun damage, skin laxity, and dermal pigmentation.

Unfortunately, however, there are many contraindications for performing deep peels with conventional phenol agents and dermabrasion. Inevitable hypopigmentation resulting from impairment of melanin synthesis in the deep peel process produces a permanent difference in the shade of the peels as compared to the untreated skin, and renders the peeled skin prone to uneven pigmentation when exposed to sunlight. Moreover, the texture and appearance of the skin of the patient being treated is also permanently altered due to the permanent destruction of hair follicles and collagen. In addition, increased risk of scarring and atrophy, or clinical loss of abnormal skin markings, is more likely to occur as an adverse side effect of a deep peel.

Furthermore, even deep peels are ineffective for correcting certain types of scars, such as deep "ice pick" scars with sharp edges and deep pits. Nor have other methods of medical treatment achieved satisfactory smoothing of such "ice pick" scars. Those treatments include dermabrasion, punch grafting and elevation (making an incision in and sewing the wound), soft tissue-filling agents such as collagen (Zyplast, Zyderm, Collagen Corp., Palo Alto, Calif.), silicone, Fibrel (commercially available from Mentor Corp., Santa Barbara, Calif.), or autologous fats, and excision. Not only are such medical procedures ineffective for flattening "ice pick" scars, there are additional problems. For instance, in applying dermabrasion, the depth of the peel is imprecise, difficult to control, and highly dependent upon the individual physician's skill in using the dermabrasion instrument. Moreover, the healing or recovery period for dermabrasion, as well as chemical peel, patients is quite long and often involves convalescence of one to three weeks or longer, as the unsightly appearance of the treated area prevents many patients from venturing outside of their homes in order to perform their normal daily routine. The smoothing effect of soft tissue-filling agents, as well as punch grafting and elevation, are notoriously short-lived, rarely lasting beyond one year and often disintegrating within the first six months after application.

Continuing dissatisfaction with existing treatment for skin problems led to further development, and, in the early 1980's, when wrinkle pharmacology based on the acceleration of exfoliation and desquamation of the skin emerged through the discovery that the acne drug Retin-A or tretinoin, removed fine lines. Since that time, a variety of exfoliation agents for reducing wrinkles have been utilized. Now, glycolic acid, salicylic acid, lactic acid, alpha hydroxy or fruit acids, as well as other exfoliants, are being incorporated in cosmetic creams in order to aid and accelerate natural cell-shedding of the skin.

Other substances have also been utilized in cosmetic compositions developed during the recent anti-wrinkle revolution. For example, ceramide creams, which are reported to repair and enhance the binding process of surface skin cells and to actively hydrate and reinforce the skin's barrier against environmental assault, have recently been formulated. Vitamin H and vitamin C are also being used in cosmetic compositions, and the manufacturers of such compositions claim that these vitamins are capable of fortifying skin cells and resisting the ill effects of the environment.

In recent years, liposomes have been used, ostensibly for transporting compounds within the inner cells of the skin, in a variety of creams, lotions, and gels manufactured by many companies.

Unfortunately, however, neither cosmetic surgical procedures nor cosmetic creams of the past have been capable of successfully preventing or correcting a lesion or crevice, particularly when it is deeply recessed in the epidermal and dermal tissue. To the contrary, there has not thus far been a substance or mechanism for carrying and delivering the foregoing and other compositions deep into the skin, particularly to penetrate hair follicles, sebaceous glands, "ice pick" scars, and other deep crevices traversing the epidermis and dermis tissue and of the skin. There is a further need for a system whereby cosmetic or medicinal agents, especially those that are intrusive, such as escharotic agents, used to treat such and other skin imperfections, which enables localization of the agent so as to prevent undesired contact of the agent with surrounding normal skin surfaces. Therefore, it is apparent that the need for a delivery system addressing such and other problems persists.

SUMMARY OF THE INVENTION

The foregoing and additional drawbacks of the prior art are addressed by the device and method of treatment for localized application of a fluid on a small area of skin, which includes an ejection nozzle forming a passage having one or more apertures with a diameter of at least between about 0.05 mm and about 5.0 mm; propulsion means for propelling the fluid through the ejection nozzle; a receptacle chamber forming a cavity around the ejection nozzle, the receptacle chamber being configured and affixed to the ejection nozzle such that fluid ejected from the ejection nozzle is capable of being confined within the receptacle chamber when placed against the skin being treated; an inflow duct forming a passage in communication with the propulsion means for delivering the fluid to the ejection nozzle; and an outflow means forming a passage which is confluent with the receptacle chamber so as to be capable of draining the fluid therefrom.

In one embodiment of the present invention, the outflow means may form a passage which returns the fluid to a reservoir from which the propulsion means repeatedly delivers fluid through the inflow duct and ejection nozzle. This embodiment thereby provides a mechanism for recirculating and reapplying the fluid applied in a semi-closed system.

The invention is further drawn toward a medical device for application of a confined stream of fluid on a skin surface, which includes the ejection nozzle, receptacle chamber, propulsion means, outflow means, and inflow duct as described above, wherein the receptacle chamber is configured and affixed to the ejection nozzle in a manner whereby the escharotic fluid propelled is capable of being confined within the receptacle chamber so as to dilate and penetrate an epithelium-lined tubular structure traversing the epidermal and dermal tissue.

In accordance with the present invention, the ejection nozzle may contain a single or multiplicity of apertures. Such apertures constitute openings at the frontal end of the ejection nozzle for facing toward the skin subject to treatment, and may number from 1 to 100, or even up to 1,000.

A further aspect of the present invention features an ejection nozzle which may be a 14 to 30 gauge cylinder, and is preferably an 18 gauge cylinder. Such a cylinder may be an appropriately gauged needle, the sharp end of which is preferably blunted or severed. The diameter of the receptacle chamber of the present invention may measure between about 1.0 mm and about 50.0 mm in diameter and is preferably between about 2 mm and about 4 min.

In one embodiment of this invention, the propulsion means is a hypodermic syringe whereby hydrostatic pressure is applied to the fluid being ejected. In a preferred embodiment of the present invention, the propulsion means includes an automated pump which is capable of continuous and repetitive propulsion of the fluid. A variety of commercially available automated pumps, including peristaltic, diaphragm and other pumps, may be used for such a propulsion means.

A preferred embodiment of the present invention may further include a vacuum means surrounding the receptacle chamber for forming a vacuum when the receptacle chamber is placed again the skin. The vacuum means thus enhances formation of a seal between the skin and the receptacle chamber and the flow of the fluid into the outflow means. The vacuum means thereby provides a safeguard against leakage of the fluid outside of the area of skin against which the perimeter of the receptacle chamber is placed.

The present invention still further provides a safety valve means for closing the passage of the inflow duct when the vacuum means is not applying suction to the vacuum tube, so as to prevent fluid from being continuously ejected capture the fluid flowing therethrough within the propulsion means. Such a safety valve means may also be actuated electronically or other means known in the art.

The present invention also provides a method of treatment of skin, which includes the steps of: propelling a fluid on a localized area of the skin, and confining the fluid within a chamber having a diameter of between about 0.5 mm and about 50.0 mm such that the area with which the fluid comes into contact is localized.

As used herein, an epithelium-lined tubular structure traversing the epidermal or dermal tissue of the skin may include a scar or pock mark, or other depression of the skin; a pore or hair follicle, and sebaceous glands; or any other such tubular structure or crevice. The scar, pore or other structure need not be a single recessed tube, but may be a tubular structure having multiple orientations, or protrude in multiple directions, in a zig-zag or other irregular manner.

The fluid utilized in the present invention may include any escharotic, i.e., a necrotizing, or caustic peeling agent, such as trichloroacetic acid, phenol, alpha-hydroxy acid, resorcinol, salicylic acid, or exfoliant, such as Retin-A or tretinoin, isotretinoin, lactic acid, pymvic acid, glycolic acid, hypertonic saline. In addition, the fluid may be a cleansing, antiseptic, moisturizing, or bleaching agent such as hydroquinone or azelaic acid.

The method of the present invention further features confining the area with which the fluid comes into contact within a chamber which is between about 1.0 mm and about 50.0 mm in diameter, and preferably confining an area within a chamber which is less than 3 mm in diameter.

The present invention is particularly effective in the treatment of depressed scars, especially deeply-pitted and sharp-edged ice pick scars, sinus tract-like lesions, and other narrow epithelium-lined passages traversing the epidermal and dermal tissue of the skin. In addition, the present invention may be used in the treatment of scarring caused by bums, abrasions, and other skin injuries, as well as acne. A further application of the present invention is in the treatment of pigmentary dyschromias, including hyperpigmented and hypopigmented areas, including melasma. Still other applications may include treating actinic, or sun-induced, keratoses; nevi; enlarged pores or philosebaceous follicles; rhytides and more pronounced wrinkles; epilations; as well as other types of skin problems.

A further advantage provided by one embodiment of the present invention which was hereinbefore unavailable is the recycling and conservation of the escharotic or other medicinal agent being applied. The recirculation and recycling of the agent being used substantially decreases the amount of the medicinal agent utilized, and thereby renders the device and method of the present invention much mote economical and efficient than previous treatments.

As further discussed below, the biophysiological mechanisms whereby the aforedescribed method and treatment minimize or obliterate depressed scars and other skin conditions include the formation of collagen, concentric contraction of skin around a wound, and the reepithelialization of the wound area which is involved in the healing process. The increased penetration and depth of injury caused by the repetitive and continuous propulsion, as well as maintaining the contact of the fluid within a small and confined area of the skin optimizes the above healing processes so as to maximize the cosmetic improvement, or smoothing, of the skin after treatment.

DETAILED DESCRIPTION OF THE INVENTION

Figure 1:
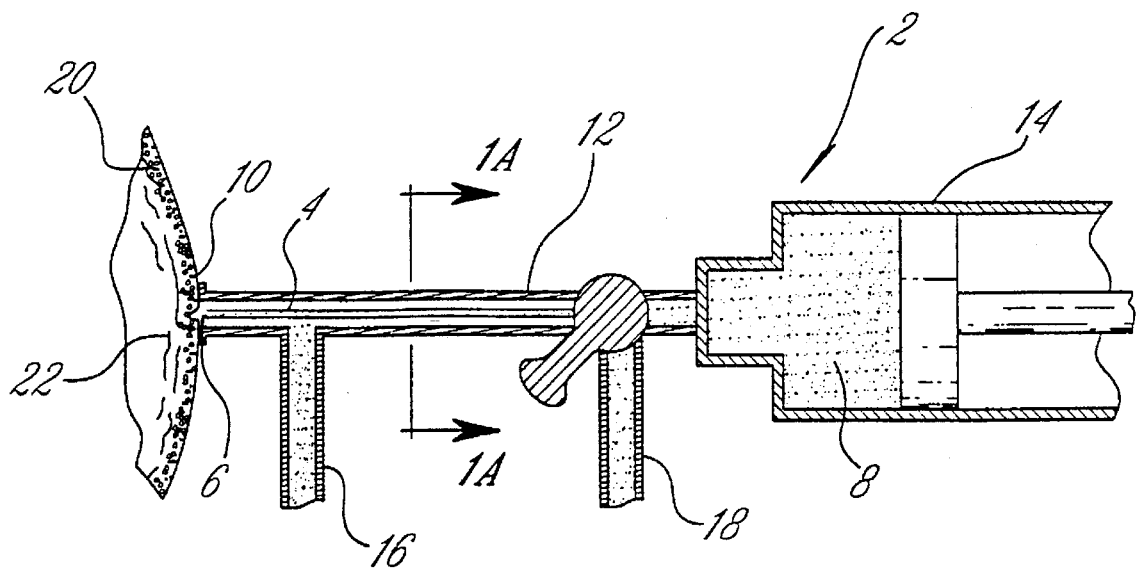
FIG. 1 provides a side cross-sectional view of the device of the present invention.
Figure 1A:
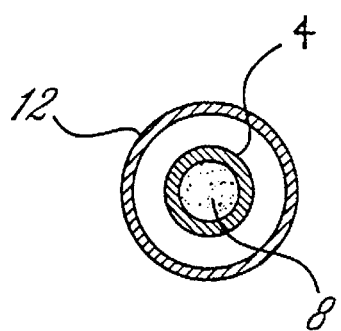
FIG. 1A depicts an exploded cross-sectional view of the device according to the present invention, taken along line 1—1 of FIG. 1.
Figure 2:
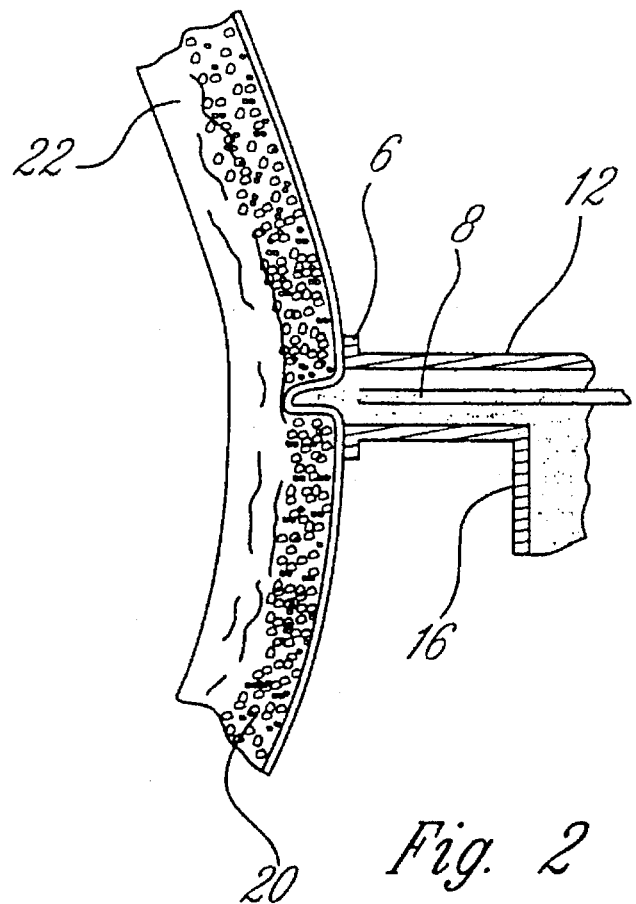
FIG. 2 provides an exploded cross-sectional view of the present invention, depicting its action upon a deep scar traversing the epidermal and dermal tissue of this skin.

Referring to the drawings, FIGS. 1 to 2 depict medical device 2, which consists of an ejection nozzle 4 forming a passage with aperture 6 for delivery of fluid 8 to skin 10. Receptacle chamber 12 forms a cavity around ejection nozzle 4 and may extend slightly beyond aperture 6 and may have a flange. Receptacle chamber 12 may be concentrically and coaxially affixed to ejection nozzle 4 in a manner whereby fluid 8 is captured and confined within receptacle chamber 12 when delivered to skin 10.

As further shown by FIG. 1, hypodermic syringe 14 may be connected to ejection nozzle 4, such that hydrostatic pressure may be continuously and repetitively delivered in order to propel fluid 8 through ejection nozzle 4. Outflow means 16 forms a passage which is confluent with inflow duct 18 and connected to receptacle chamber 12 and thereby drains the fluid 8 therefrom. Inflow duct 18 is similarly confluent with and connected to outflow means 16 in a manner whereby fluid 8 may be channeled into hypodermic syringe 14 whereupon fluid 8 may be propelled again through ejection nozzle 4 and onto skin 10. Also shown is a means for closing the passage of the inflow duct 18 so as to capture the fluid within the propulsion means by a sprocket valve, which is affixed to inflow duct 18 such that fluid 8 is reintroduced into hypodermic syringe 14 when it is not engaged in the action of propelling fluid 8 through ejection nozzle 4.

After thus applying fluid 8 on skin 10 with the device of the present invention shown in FIGS. 1–2, fluid 8 is captured and confined within receptacle chamber 12 and may be swirled therein in a manner whereby fluid 8 continues to be placed in contact with the skin within the walls of receptacle chamber 12. Such confinement of fluid 8 increases penetration and the depth of contact with the skin 10.

Figure 3:
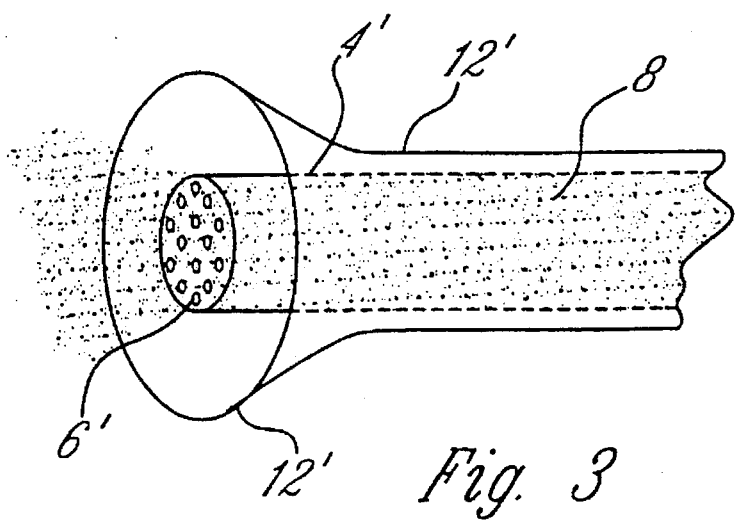
FIG. 3 depicts a perspective view of the device according to the present invention having a multiplicity of apertures.

When escharotic agent is applied according to the present invention, portions of the epidermal tissue 20 and underlying dermal tissue 22, as well as, the walls of epithelium-lined tubular structure 24 are destroyed. Epithelium-lined tubular structure 24 may be a pore, hair follicle, ice pick scar, or other crevice traversing the epidermal and dermal tissue. The localization of the escharotic agent combined with the repetitive and continuous propulsion of fluid 8 increases penetration and the depth of injury to the skin contacted so as to destroy portions of the epidermis 20 and underlying dermal tissue 22 contacted.

Where fluid 8 contains an escharotic fluid, the manner of wounding the scar and skin directly surrounding the scar promotes healing wherein the formation of collagen, concentric contractions of the skin around the wound, and the reepithelialization of the wounded area maximizes the filling in, or smoothing, of the scar treated so as to minimize or even obliterate the FIG. 3 depicts another embodiment of the present invention, which is configured and operates in a similar manner to the device illustrated in FIGS. 1 to 2, except that ejection nozzle 4' has a multiplicity of apertures 6' for ejection of fluid 8', and is affixed and connected to receptacle chamber 12' so that fluid 8' is capable of being confined within the walls of the receptacle chamber 12' when the device is placed upon the skin being treated. Fluid 8' is thus propelled and delivered to the skin being treated. Fluid 8' may contain any medicinal agent, including, but not limited to, an exfoliant such as Retin-A, lactic acid, pyruvic acid, isotretinoin, glycolic acid, or hypertonic saline; a cleansing, antiseptic or moisturizing agent; or bleaching agent such as hydroquinone or azelaic acid.

Figure 4A:
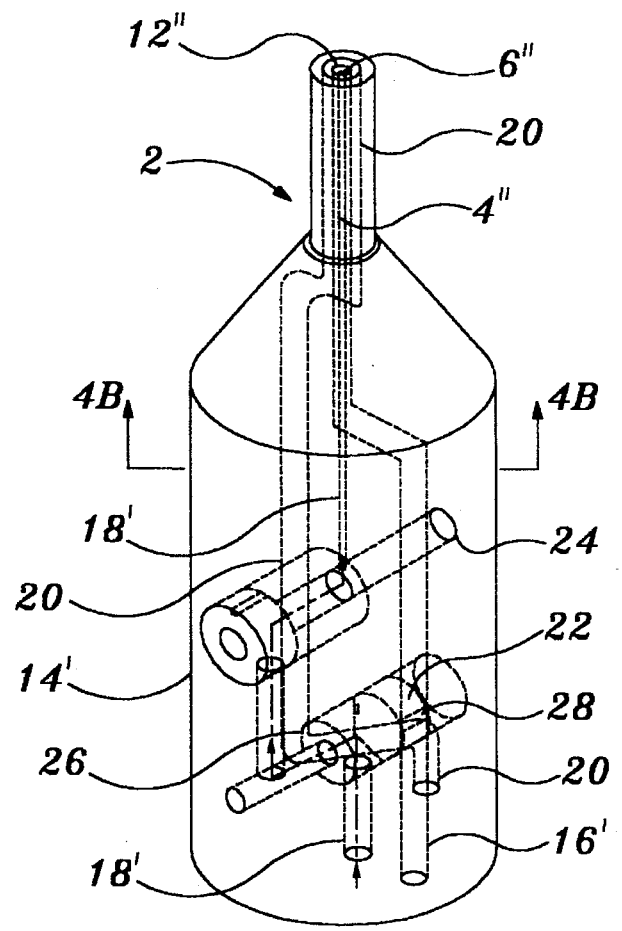
FIG. 4A provides a cross-sectional view, taken along line 4A—4A of FIG. 4.
Figure 4B:
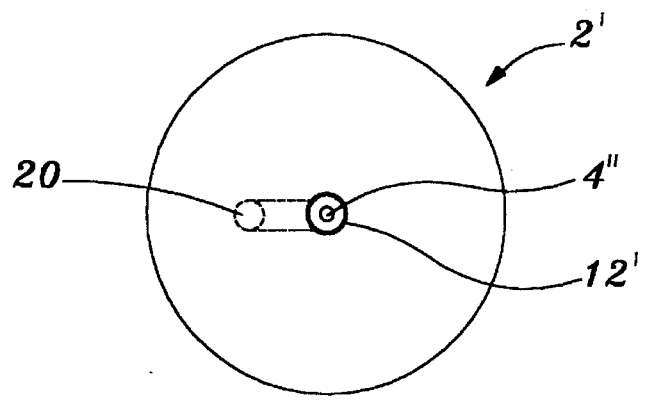
FIG. 4 illustrates a side perspective view of an embodiment of the present invention including a safety valve means and vacuum means.

Now referring to FIGS. 4 and 4A, automated medical device 2' includes propulsion means 14', which may be a variety of pumps, such as, for example, a peristaltic or diaphragm pump. Propulsion of fluid 8 from ejection nozzle 4' is effected by applying downward pressure on push button valve means 24. Due to the similar diameters of cone 26 and the corresponding cone-shaped surface in the passage where it interfaces with cone 26, a seal is formed at the interface which obstructs flow of fluid 8 when push button valve means 24 is not compressed, i.e., is in the off position. Compression of push button valve means 24 dislodges the obstructing seal, and fluid 8 then flows through channel 28. Fluid 8 is thus continuously delivered to inflow duct 18' so long as push button valve means 24 is depressed and ejection nozzle 4" is placed against skin 10 so as to form a vacuum exerting outward pressure which disengages safety valve means 22 from obstruction of flow of fluid 8 through inflow duct 18', as further described below. Push button valve means 24 constitutes just one of many possible modes for actuation of the device shown, which could, of course, be actuated by many alternative mechanisms.

After being propelled through ejection nozzle 4', fluid 8 contacts skin 10 and enters outflow means 16' and drains into a reservoir from which fluid 8 is delivered to inflow duct 18'. A system for recirculation of fluid 8 is thus provided by the present invention.

Automated medical device 2' further includes vacuum means 20 which applies suction to the ejection nozzle, and thereby minimizes leakage of fluid 8 outside of the perimeter of receptacle chamber 12" when applied to the skin 10. Utilization of vacuum means 20 is particularly desirable when applying escharotic or other caustic agents to the skin, as contact of such agents with areas of the skin not being treated may be contraindicated.

Activation of vacuum means 20 also controls safety valve means 22, which is seated so as to obstruct flow of fluid 8 through inflow duct 18' when there is no vacuum pressure applied, i.e., there is no seal being formed between skin 10 and receptacle chamber 12". When vacuum pressure is effected through placement of receptacle chamber 12" upon skin 10, vacuum means 20 pulls safety valve means 22 against the outside of the assembly and away from inflow duct 18' toward ejection nozzle 4". Safety valve means 22 is thus dislodged to a position which does not obstruct passage of fluid 8 through inflow duct 18' and fluid 8 is continuously propelled through aperture 6' of ejection nozzle 4".

Figure 5:
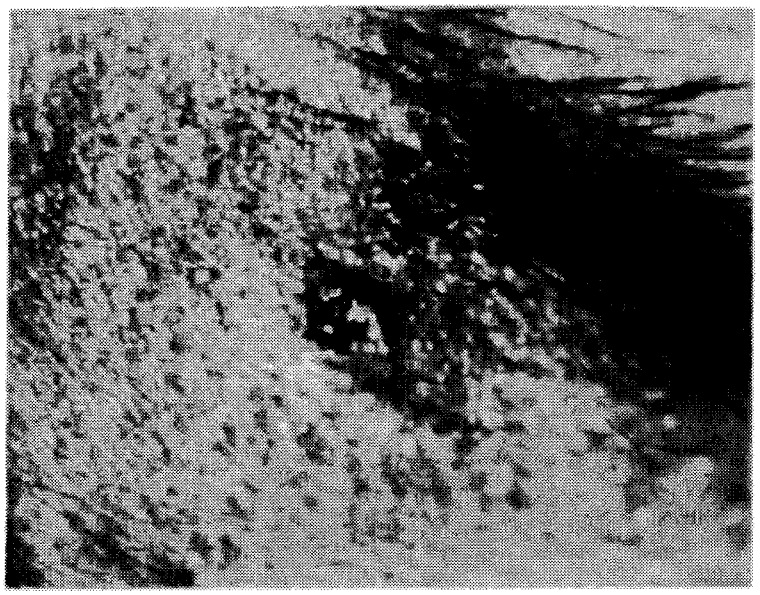
FIG. 5 provides a photograph taken before treatment according to the present invention.

The efficacy of the aforedescribed device and method of treatment for scars and other skin anomalies was demonstrated in a case study performed upon a 23-year-old white male. As shown in the photograph in FIG. 5, taken before treatment according to the present invention, the male subject presented with a deep-pitted, sharp-edged ice pick scar measuring about 5 mm in depth.

This scar was treated by continuously delivering 10 ml of a solution containing 41.6% of trichloroacetic acid which was propelled through an 18 gauge needle by a hypodermic syringe through continuous and repeated propulsions of approximately 10 ml of fluid. The fluid was then captured, confined, and swirled within a receptacle chamber in the form of a cannula with a diameter of about 3 mm, which was fitted around the needle. The fluid was then recirculated it through an outflow means and then delivering the fluid again into the syringe through an inflow duct. The 10 ml fluid was repeatedly propelled against the target skin surface at the orifice of the ice pick scar in order to dilate and penetrate the depression.

Figure 6:
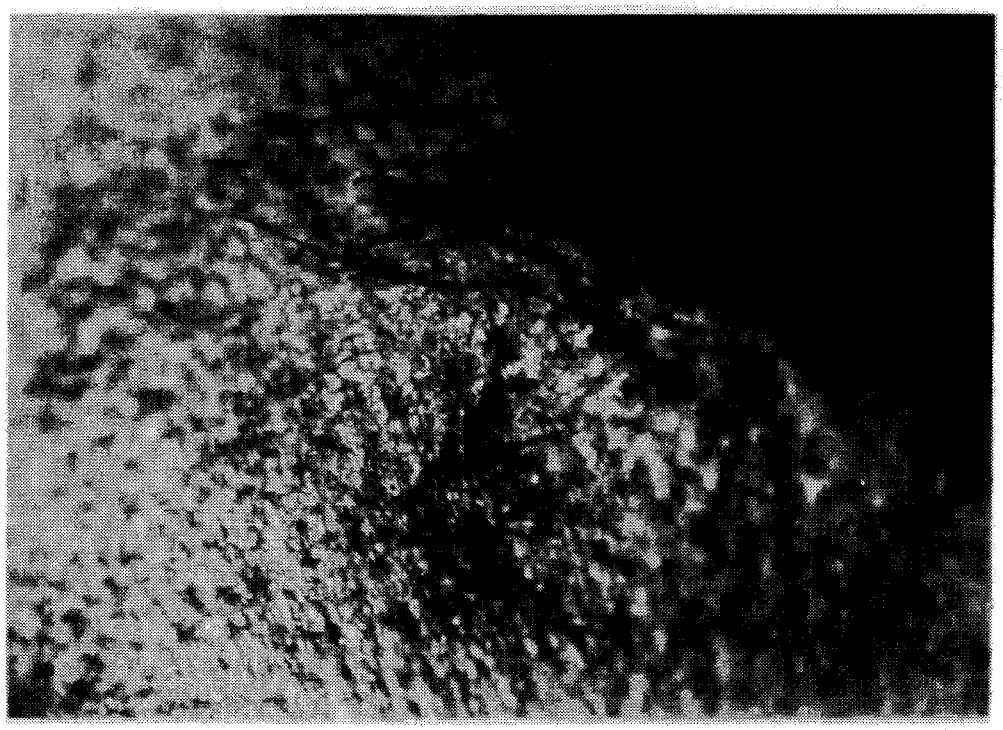
FIG. 6 provides a photograph taken 30 days after treatment according to the present invention.

As shown in the photograph in FIG. 6, taken 30 days after thus treating the male subject, the healing of the wound resulting from the above treatment produced virtually complete obliteration of the deeply recessed scar.

It is to be understood that the present invention is not intended to be limited to the exact details of construction, operation, exact materials, or embodiment shown and described herein, as obvious modifications and equivalents will be apparent to one skilled in the art of treating skin anomalies. For example, the device and method of the present invention could be applied to any abnormal growth, lesion, blemish, or other undesirable disfigurement or marking, such as varicose veins or epilations, on the skin. Moreover, the fluid applied by this invention may include any therapeutic agent, such as an exfoliant, antiseptic solution, or other medicinal agent. This disclosure is intended to cover all alternatives, modifications, and equivalents as may be included within the spirit and scope of the invention as defined by the appended claims.

The following claims represent the scope of this invention to the extent that it is subject to such delimitations. It will be appreciated by those skilled in the art that the anticipated uses and embodiments of the present invention are not amenable to precise delineation, but may vary from the exact language of the claims. Thus, the following claims are drawn not only to the explicit limitations, but also to the implicit embodiments embraced by the spirit of the claims.

What is claimed is:

1. A medical device for localized topical application of a fluid on a small area of skin, comprising:
   a. an ejection nozzle forming a passage and having one or more apertures with a diameter of at least between about 0.05 and about 5.0 mm, the ejection nozzle being capable of propelling fluid on skin;
   b. a propulsion means in communication with the ejection nozzle so as to be capable of propelling fluid therethrough;
   c. a receptacle chamber extending forwardly in a sleeve surrounding the ejection nozzle, the receptacle chamber opening into an outer perimeter so as to confine fluid delivered from the ejection nozzle within the perimeter of the receptacle chamber when placed against the skin;
   d. an inflow duct in fluid communication with the ejection nozzle, the inflow duct forming a passage for delivering fluid from a fluid source to the ejection nozzle; and
   e. an outflow means forming a passageway which is confluent with the receptacle chamber for draining the confined fluid through the passageway.

2. The medical device of claim 1, wherein the ejection nozzle is a 14 to 30 gauge cylinder.

3. The medical device of claim 1, wherein the receptacle chamber measures between about 0.5 mm and about 50.0 mm.

4. The medical device of claim 1, wherein the propulsion means comprises an automated pump which is capable of continuous and repetitive propulsion of the fluid.

5. The medical device of claim 1, further comprising a switch means the actuation of which simultaneously opens the inflow duct and propels the fluid by the propulsion means.

6. The medical device of claim 1, further comprising a vacuum means surrounding the receptacle chamber for forming a vacuum when the receptacle chamber is placed against the skin such that flow of the fluid through the outflow means is enhanced.

7. The medical device of claim 1, further comprising a safety valve means for closing the passage of the inflow duct so as to prevent the fluid from being continuously delivered to the propulsion means when no fluid is being propelled through the ejection nozzle.

8. The medical device of claim 1, wherein the inflow duct forms a passage confluent with the outflow means so as to be capable of returning the fluid to a reservoir wherefrom the fluid is available for propulsion through the ejection nozzle.

9. The medical device of claim 1, wherein the fluid propelled is capable of being confined within the receptacle chamber so as to dilate and penetrate an epithelium-lined tubular structure traversing the epidermal and dermal tissue.

10. A method for localized topical application of fluid to a small area of skin, comprising the steps of:
    a. placing an ejection nozzle having a receptacle chamber extending forwardly in a sleeve surrounding the ejection nozzle so as to capture fluid delivered from the ejection nozzle within the perimeter of the receptacle chamber;
    b. propelling fluid on the skin;
    c. confining the fluid within a receptacle chamber having a diameter of between about 0.5 mm and about 50.0 mm so as to localize the area in which the fluid comes into contact with the skin; and d. draining the fluid from the receptacle chamber through an outflow duct.

11. The method of claim 10, wherein the fluid is further propelled into an epithelium-lined tubular structure traversing epidermal and dermal tissue of the skin so as to penetrate and transport the fluid into the epithelium-lined tubular structure.

12. The method of claim 10, wherein the fluid comprises an escharotic fluid.

13. The method of claim 10, wherein the fluid comprises trichloroacetic acid.

14. The method of claim 10, wherein the fluid comprises phenol.

15. The method of claim 10, wherein the fluid comprises an alpha hydroxy acid.

16. The method of claim 10, wherein the fluid comprises resorcinol.

17. The method of claim 10, wherein the fluid comprises lactic acid.

18. The method of claim 10, wherein the fluid comprises pyruvic acid.

19. The method of claim 10, wherein the fluid comprises glycolic acid.

20. The method of claim 10, wherein the fluid comprises an exfoliant.

21. The method of claim 10, wherein the fluid comprises tretinoin.

22. The method of claim 10, wherein the fluid comprises isotretinoin.

23. The method of claim 10, wherein the fluid comprises hypertonic saline.

24. The method of claim 10, wherein the fluid comprises a medicinal agent.

25. The method of claim 10, wherein the fluid comprises a cleansing agent.

26. The method of claim 10, wherein the fluid comprises an antiseptic agent.

27. The method of claim 10, wherein the fluid comprises a moisturizing agent.

28. The method of claim 10, wherein the fluid comprises a bleaching agent.

29. The method of claim 10, wherein the fluid comprises a hydroquinone.

30. The method of claim 10, wherein the fluid comprises an azelaic acid.

31. A medical device for localized topical application of a fluid on a small area of skin, comprising:

a. an ejection nozzle forming a passage and having one or more apertures with a diameter of at least between about 0.05 and about 5.0 mm, the ejection nozzle being capable of propelling fluid on skin; and b. a receptacle chamber extending forwardly in a sleeve surrounding the ejection nozzle, the receptacle chamber opening into an outer perimeter so as to confine fluid delivered from the ejection nozzle within the perimeter of the receptacle chamber when placed against the skin.

32. The ejection nozzle of claim 31, wherein the receptacle chamber measures between about 1.0 mm and about 50.0 mm.

* * * * *